United States Patent [19]

Cox et al.

[11] Patent Number: 5,150,706

[45] Date of Patent: Sep. 29, 1992

[54] COOLING NET FOR CARDIAC OR TRANSPLANT SURGERY

[76] Inventors: James L. Cox, 7 Dromara Rd., Ladue, Mo. 63124; Robert D. B. Jaquiss, 465 Fourwynd, Creve Coeur, Mo. 63141

[21] Appl. No.: 745,519

[22] Filed: Aug. 15, 1991

[51] Int. Cl.$^5$ .............................................. A61F 7/00
[52] U.S. Cl. ................................. 128/400; 128/401; 128/402; 128/897; 600/37; 604/49; 604/113
[58] Field of Search .................... 606/20, 21; 604/49, 604/113, 291; 128/850, 897-898, 399-403; 602/4, 60-61, 75-76; 600/37

[56] References Cited

U.S. PATENT DOCUMENTS

| | | | |
|---|---|---|---|
| 3,091,242 | 5/1963 | Johnson, Jr. et al. | 128/402 |
| 3,983,863 | 10/1976 | Janke et al. | 600/37 |
| 4,010,795 | 3/1977 | Stenberg | 165/46 |
| 4,154,245 | 5/1979 | Daily | 128/400 |
| 4,259,961 | 4/1981 | Hood, III | 128/400 |
| 4,416,281 | 11/1983 | Cooper et al. | 128/400 |
| 4,474,016 | 10/1984 | Winchell | 62/60 |
| 4,971,056 | 11/1990 | Seacord | 128/401 |
| 5,014,695 | 5/1991 | Benak et al. | 128/400 |

OTHER PUBLICATIONS

Bonchek, L. I. and Olinger, G. N., "An improved method of topical cardiac hypothermia," *J. Thorac. Cardiovasc. Surg.* 82: 878-882 (1981).

Daily, P. O., et al., "Clinical comparisons of methods of myocardial protection," *J. Thorac. Cardiovasc. Surg.* 93: 324-336 (1987).

Daily, P. O., et al., "Comparison of myocardial temperatures with multidose cardioplegia versus single-dose cardioplegia and myocardial surface cooling during coronary artery bypass grafting." *J. Thorac. Cardiovasc. Surg.* 97: 715-724 (1989).

Daily, P. O. and Kinney, T. B., "Optimizing myocardial hypothermia: II. Cooling jacket modifications and clinical results," *Annals Thorac. Surg.* 51: 284-289 (1991).

Rosenfeldt, F. L. and Arnold, M., "Topical cardiac cooling by recirculation: Comparison of a closed system using a cooling pad with an open system using a topical spray," *Annals Thorac. Surg.* 34: 138-145 (1981).

*Primary Examiner*—C. Fred Rosenbaum
*Assistant Examiner*—C. Maglione
*Attorney, Agent, or Firm*—Patrick D. Kelly

[57] ABSTRACT

This invention provides a device and method for cooling an internal organ during surgery. The device involves a porous, water-permeable net, preferably made of hydrophilic elastic fabric. The net is fitted and secured around the organ and cold saline solution is infused into the net, preferably by means of a side-hole catheter. The cold liquid passes through the net, directly contacting and chilling the organ. As the liquid drips out of the net, it is removed from the patient's chest or abdomen by suction tube. To provide convenient access to any location on the surface of the organ (for example, to operate on a coronary artery which must be bypassed) a cut is made through a part of the net overlying the location that must be operated on. This exposes the artery without affecting the ability of the net to cool the rest of the organ. The cooling net described herein also provides a method of cooling the atrial region of a heart during surgery, by means of a segment of porous tubing positioned in the atrial region of the heart. Part of the cold liquid diffuses out of the porous tubing and chills the atrial region, while the rest of the cold liquid permeates through the net and chills the ventricular region.

13 Claims, 4 Drawing Sheets

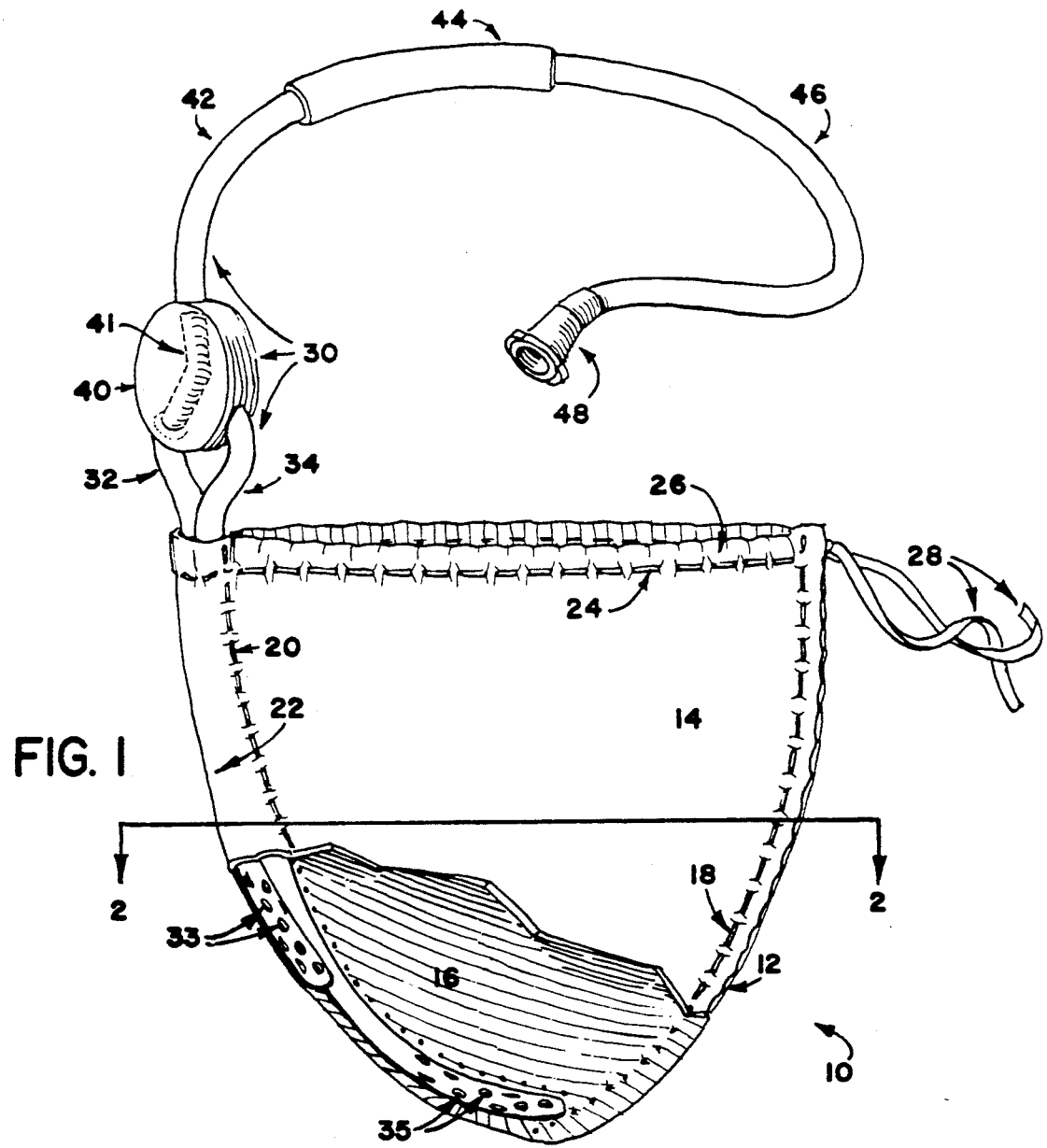
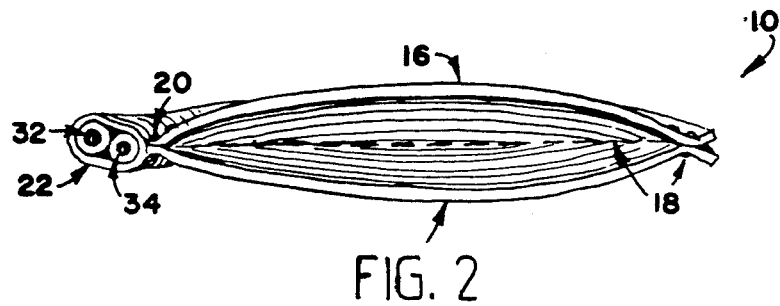

COOLING NET FOR CARDIAC OR TRANSPLANT SURGERY

This invention is in the field of surgical devices, and relates to a device used during heart surgery and organ transplantation.

Since cardiac surgery is more common than organ transplant surgery, the sections below will focus first on cardiac surgery, then on organ transplantation.

Most cardiac surgical procedures are performed with the heart arrested and excluded from the circulation. This provides a motionless organ with no blood actively flowing through its arteries and veins, which greatly facilitates surgery. The state of bloodless arrest is made possible by several interventions. An artificial blood pump and oxygenator (called cardiopulmonary bypass) is provided to substitute for the heart and lungs during the period of arrest. The heart is excluded from the circulation by clamping the aorta just above the coronary arteries. Cardiac arrest is then accomplished by delivering into the coronary arteries and/or coronary veins a special chemical solution called cardioplegia.

These interventions impose a significant burden on the heart. While the heart is not being perfused with blood, it is denied the oxygen and nutrients necessary to support cardiac metabolism. The negative consequences of inadequate oxygen supply may be greatly ameliorated by decreasing oxygen demand and minimizing cardiac metabolism during the period of arrest, which is achieved by cooling the heart to a low temperature, usually in the range of about 8 to 15 degrees centigrade.

Cooling is accomplished in two ways (which may be used alone, but which preferably should be used in conjunction). One method involves cooling the heart from within, by circulating a cold solution through the arteries and veins; this is usually called perfusion cooling, and there are several types of perfusion cooling, discussed below. The other method involves cooling the external surfaces of the heart with chilled solutions or devices; this approach is usually called topical hypothermia.

Perfusion cooling (reviewed in Daily et al 1987) is most commonly accomplished by using chilled cardioplegia solution and delivering it via the coronary arteries (antegrade cardioplegia), which both stops and cools the heart. However, this method does not effectively cool the portion of the heart which is supplied by coronary arteries that are partially or completely occluded (a universal circumstance in all coronary artery bypass operations). Furthermore, the cooling which is accomplished is of finite duration. As soon as the infusion of cold solution into the heart stops, the heart begins to warm up again, primarily because of heat influx from surrounding body tissues, which are customarily in the range of 26° to 30° C.

Under the prior art, the only way to adequately maintain the temperature of the heart in the preferred range during most types of surgical operations (such as coronary bypass operations) was to repeat the perfusion process. In some cases, the cooling/warming cycle is repeated several times during surgery, thus interrupting the operation and prolonging the period of cardiac arrest.

Perfusion cooling may also be accomplished by delivering chilled cardioplegia via the coronary veins; this is called retrograde cardioplegia. This method can cool areas of the heart supplied by blocked arteries, but it is relatively less effective at cooling the right ventricle and possibly the deepest layers of cardiac muscle. Like antegrade cardioplegia, it must be repeated often to provided prolonged effective cooling.

Both methods of cardioplegia (antegrade and retrograde) also suffer from an additional major limitation: they do not effectively cool the atria or atrial septum of the heart. This limitation has been shown in clinical and experimental studies to result in significant post-operative disorders of cardiac electrical conduction and rhythm in many patients.

To overcome some of the limitations discussed above, perfusion cooling is most commonly combined with some form of topical hypothermia. The simplest method of topical cooling is to pour iced saline (often in the form of a slush) directly onto the exposed surface of the heart during surgery. This is easily accomplished, but it is imprecise and difficult to control. Furthermore, direct application of iced slush into the open chest around the heart can sometimes cause permanent injury to the nerves supplying the diaphragm, causing diaphragmatic paralysis (Rousou et al 1985). In addition, as with perfusion methods, iced slush must be administered repeatedly in order to maintain the temperature in the desired range, but repeated applications interrupt and prolong surgery and the period of arrest. An additional limitation of topical hypothermia is that its use blocks direct access to the surface of the heart, where coronary artery bypass surgery is performed.

Another means of delivering topical hypothermia is to wrap the heart with iced slush-soaked surgical gauze. This is less likely to injure the diaphragmatic nerves than iced slush itself, but in many situations it would prevent necessary access to the surface of the heart, so it cannot be used except for brief periods.

A third method of topical cooling, often called the Shumway technique, involves continuous infusion of chilled saline into the cavity that is created when the pericardium is opened to expose the heart (Shumway and Lower 1959; also see Daily 1987 and Rosenfeldt and Watson 1978). In this method, an infusion catheter supplies a continuous stream of chilled liquid into the pericardial basin (also called a cradle or a sling). A suction catheter is sutured to the pericardial wall at an elevation which allows a substantial quantity of cold liquid to stand in the pericardial basin, effectively submerging part of the heart during the surgery. Although this technique avoids repeated interruptions of surgery, it unfortunately does not efficiently cool the posterior surface of the heart, which rests on the warm pericardial membrane, or any portion of the heart which is not submerged in the cold liquid. In addition, it provides no effective atrial cooling.

A fourth type of topical hypothermia involves devices known as cooling jackets, described in Bonchek and Olinger 1981, and in Daily et al 1987, 1989, and 1991. Several such jackets are commercially available from Shiley Inc. (Irvine, Calif.), Cobe Inc. (Lakewood, Colo.) and Cardiomed Supplies (Gormely, Ontario, Canada). In essence, each of these devices consist of a closed, hollow plastic jacket which is wrapped around the ventricular portion of the heart. A continuous stream of chilled solution is pumped through the plastic jacket. The chilled liquid never leaves the plastic device or directly contacts the surface of the heart. As with other topical methods however, cooling jackets prevent access to the surface of the heart. Therefore, they cannot be used for coronary artery bypass surgery. In addition, they provide no atrial cooling.

Thus, all of the methods and devices taught by the prior art suffer from important limitations in their effectiveness, including: (1) they can limit access to the surface of the heart, (2) they can be of inadequate duration and require re-application or re-administration, and (3) they provide inadequate cooling of the atria and atrial septum.

Cooling During Organ Transplantation

As used herein, "organ" refers to an internal organ made of solid, cohesive tissue, such as a heart, liver, kidney, lung, or pancreas. This distinguishes organs and organ transplantation from operations involving other cells or tissue, such as bone marrow or islet cell transplantation.

During transplantation, an organ is excluded from its blood supply from the time its artery(s) is interrupted when harvesting the organ from the donor, until the artery is reconnected to the blood circulation of the recipient. In many transplantation procedures, that period has three separate components. The first component occurs during the surgery to remove the organ from the donor. The second component, which can sometimes last for a day or longer, involves storing the organ until a recipient is ready for surgery. The third component begins when the implantation surgery begins; it lasts until circulation is restored in the recipient.

In other types of surgery, such as coordinated kidney donations where both the donor and the recipient are prepared at the same time and are operated on at the same time, the middle component is eliminated, and the organ is excluded from circulation only during the removal and implantation surgery.

Until now, there has been no adequate means for effectively cooling an organ during the implantation procedure. Perfusion and topical cooling can be effectively used to cool an organ during removal surgery, and after the organ has been removed, containers such as ice chests or refrigerated compartments can chill and even perfuse organs that are outside the body. However, such storage techniques stop working as soon as the organ is lifted out of the container and the implantation surgery begins. Since implantation can take roughly 30 to 40 minutes for uncomplicated procedures such as kidney transplants, and well over an hour for more complicated procedures such as heart or lung transplants, this can subject an organ to substantial rewarming while it is not receiving any blood supply.

The current methods of suppressing premature and harmful rewarming during organ implantation are currently limited to topical means, which usually involve pouring on iced slush, or wrapping the organ in chilled gauze. Both methods are unwieldy; the application of slush interrupts surgery and prolongs the phase of reestablishment of flow, and the use of gauze wrapping impedes access to the organ. Accordingly, an improved device and method are needed for maintaining internal organs at chilled temperatures during implantation in a recipient.

One object of this invention is to provide a device and method for continuous effective cooling of the heart during heart surgery, which requires no interruption or prolongation of surgery, and which prevents unwanted warming or temperature cycling.

Another object of this invention is to provide a device and method for continuously cooling the heart during surgery which allows direct access to any desired portion of the surface of the heart, and which can be used during operations such as coronary bypass surgery.

Another object of this invention is to provide direct and effective cooling of the atrial portion of the heart.

Another object of this invention is to provide a method and device which may be used to continuously and effectively cool a transplanted organ such as a kidney, liver, heart, lung, or pancreas during removal or implantation surgery, without impeding surgical access to the surfaces of the organ.

SUMMARY OF THE INVENTION

This invention provides a device and method for cooling an internal organ during surgery. The device involves a woven or knitted, porous, water-permeable net, preferably made of hydrophilic fibers to promote capillary diffusion of water throughout the entire net during use. The net is fitted and secured around the organ, and cold saline solution is infused into the net, either continuously by means such as a side-hole catheter secured in or to the net, or intermittently if desired. The cold liquid passes through the net, directly contacting and chilling the surface of the organ. When it leaves the net, the liquid is removed from the patient's chest or abdomen by suction tube. To provide convenient access to any desired location on the surface of the organ (for example, to operate on a coronary artery which must be bypassed) a cut is made through a part of the net overlying the location that must be operated on. This exposes the artery or other desired region without affecting the ability of the net to carry and diffuse cooling solution throughout the remainder of the net. This invention also teaches a method of cooling the atrial region of a heart during surgery. Before reaching the exit holes of an infusion catheter in the ventricular region, the cold liquid passes through a segment of porous tubing positioned in the atrial region of the heart. Part of the cold liquid diffuses out of the tubing through the porous segment and chills the atrial region, while the rest of the cold liquid permeates through the net and chills the ventricular region.

BRIEF DESCRIPTION OF THE DRAWINGS

FIG. 1 is a front view of a cooling net having a double-lumen catheter for heart surgery.

FIG. 2 is a top cross-sectional view of the net when not in use, after it has been opened up slightly to show the front and back walls.

DETAILED DESCRIPTION OF THE PREFERRED EMBODIMENTS

Figure 3:
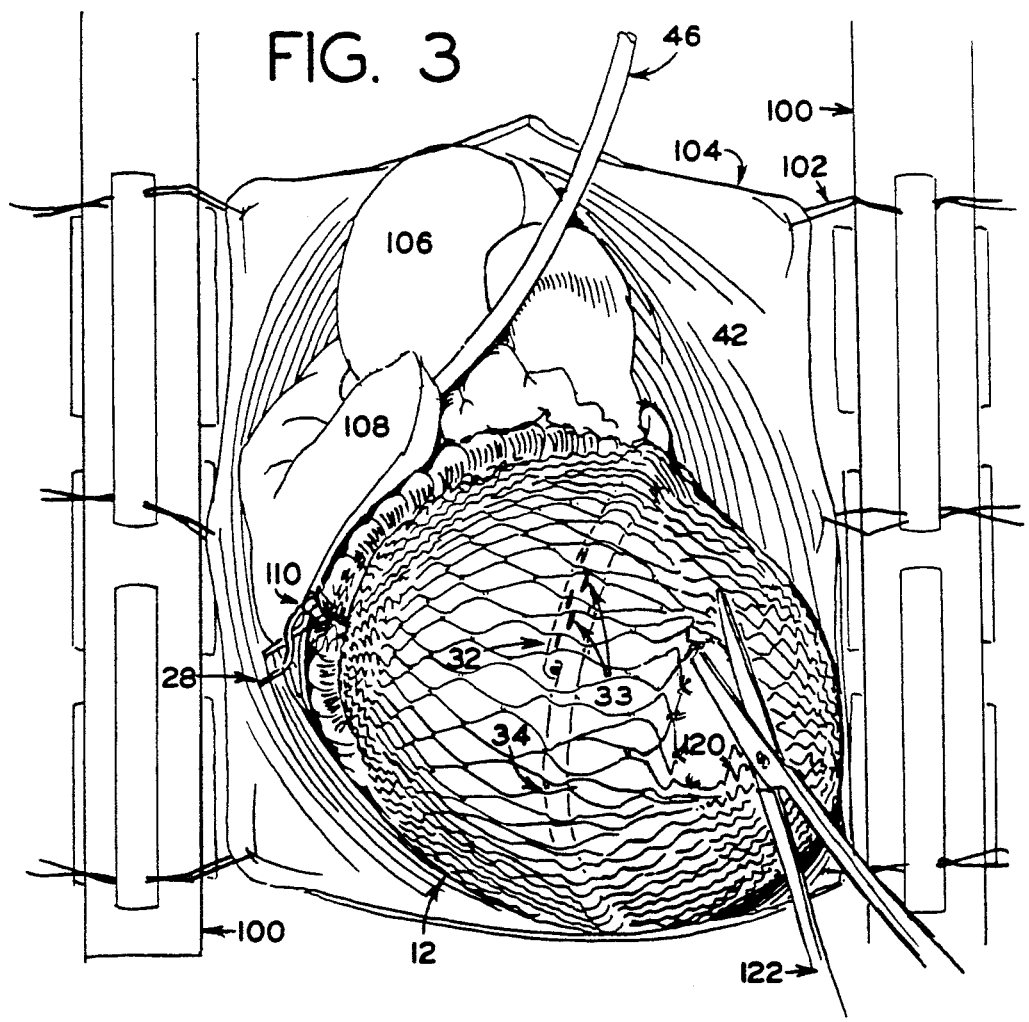
FIG. 3 is a perspective view of the cooling net after it has been fitted over the ventricular region of a heart and secured with a drawstring.

This invention provides a device and a method for cooling an internal organ during surgery. The device comprises a net made of a porous, water-permeable fabric. The net is secured around the surface of an internal organ. When in place during surgery, a cooling liquid such as cold saline solution is infused into the fabric of the net. The cold liquid is not enclosed within the net; instead, it diffuses through the net (aided by both gravity and capillary flow) and directly contacts the surface of the organ. As the liquid leaves the net, it is removed from the patient's chest or abdomen by means such as a suction tube. In effect, the net directs the flow of the cold liquid around the surface of the organ. This keeps the liquid in contact with the surface of the organ, thereby chilling the organ.

Although physiological saline solution is preferred, various types of non-aqueous fluids are also available which are relatively inert and non-toxic. Such fluids can be used for the purposes of this invention if desired, provided that the chosen fluid has the proper flow characteristics.

One of the primary advantages of this system is that a cut can be made in any specific region of the net, to expose a limited area of the organ underlying the location of the cut. This renders structures the surface of the organ accessible to a surgeon at that particular location. This allows the surgeon to carry out a procedure such as bypassing a specific coronary artery, without interfering with the ability of the net to cool the remainder of the organ. It also allows easy access to the blood vessels supplying donor organs such as the lung or kidney without interfering with the ability to cool the parenchyma of the organ during implantation into a recipient.

Cooling Net for Heart Surgery

One preferred embodiment of the cooling net of this invention is suitable for use during heart surgery, as depicted in FIGS. 1 through 6. This embodiment comprises a cooling net assembly 10 having a pocket component 12 and a tubing assembly 30. FIG. 1 depicts net assembly 10 in an empty and relaxed flat configuration when not in place around a heart; FIG. 2 is a top cross-sectional view of the pocket after it has been opened slightly.

The pocket 12, which preferably is made of an elastic fabric as discussed below, comprises a front wall 14, and a back wall 16. In one preferred manner of construction, this pocket is made by folding a flat piece of fabric once and sewing the two sides together by a main enclosure seam 18 (stitched seams are represented in the drawings by dotted lines), to form a pocket that is closed at the bottom and open at the top. In an alternate method of construction, a piece of fabric knitted in a tubular configuration (comparable to a sock) can be used as the starting piece of material. In a third configuration, two pieces of fabric can be placed flat against each other and sewn together. Other arrangements also can be used if desired, so long as the net can be secured in a comforming manner around a heart during surgery, in direct contact with the surface of the heart. For example, a flat or contoured piece of fabric can be secured in place around a heart (or other internal organ) by means of Velcro strips, elastic bands coupled to alligator clips, or other comparable means.

A catheter seam 20 creates a catheter sleeve 22 which runs along most of the length of the side of pocket 12. Since the prototypes made for testing purposes were sewn by hand, the catheter sleeve 22 was made by sewing catheter seam 20 near the middle of the initial piece of fabric. This placed the catheter sleeve at the opposing side of the pocket from the main structural seam 18. If desired, the catheter sleeve can be combined with the main structural seam, placing both on a single side of the pocket 12.

In order to secure the pocket 12 to the heart during surgery, a drawstring seam 24 can be used to create a drawstring sleeve 26 at or near the opening of the pocket 10. The drawstring sleeve 26, which preferably should pass around the entire mouth of the pocket, encloses a drawstring 28, which is tightened and tied around the atrio-ventricular groove region of the heart after the pocket has been fitted over the heart during surgery, as shown in FIG. 3. This firmly secures the net around the heart. Alternately, an elastic band or Velcro segments could be sewn onto one or more portions of fabric around the mouth of the pocket or in some other suitable location.

The catheter sleeve 22 encloses at least one infusion catheter and preferably encloses two infusion catheters, a short segment 32 and a long segment 34, both of which are part of tubing assembly 30. Both segments can be provided by a single piece of double-lumen tubing, or by placing two separate pieces of tubing next to each other inside the catheter sleeve 22. Short catheter segment 32 has a plurality of side holes 33, while long catheter segment 34 has a plurality of side holes 35. Each catheter is closed at its end, by means such as heat-crimping.

The tubes used in prototype nets during surgery were relatively slender and had an outside diameter of about 3 mm and an inside diameter of roughly 1 mm. These provided adequate flow capacity without obstructing surgery or presenting problems of stiffness. Such tubing is commercially available, with or without side holes already passing through it, from companies such as Terumo (Somerset, N.J.) or Becton-Dickinson Labware (Lincoln Park, N.J.). If no holes are present in the purchased tubing, they can be created by passing a solid needle having a round cross-section through both walls of the tubing along the desired outlet region several times. If a flat blade or the point of a hypodermic needle is used to make the holes, care should be taken so that the elongated incisions will be oriented along the length of the tubing, rather than transversely, which might weaken the tubing.

The two segments preferably should be coupled to a manually operable valve 40, which when properly operated will allow either the short catheter segment 32 or the long catheter segment 34 to receive fluid from tubing segment 42, which is coupled to a permeable atrial cooling segment 44, discussed below. Permeable segment 44 is coupled to supply tube 46, which is fitted with a coupling device 48 to allow the entire tubing assembly 30 to be coupled in fluid communication to a source of chilled liquid.

Valve 40 preferably should have a clear plastic housing so that the position of interior channel 41, which directs flow to either of the catheter segments 32 or 34, is readily visible at any time. Various types of valves having suitable dimensions are commercially available; for example, a sterile valve having a piston-type actuator, which receives fluid through a middle tube and routes the fluid to either of two outlet tubes, depending on the position of the piston, is sold for use during heart surgery in Cardioplegia System No. CPS1000 by Gish Biomedical Inc. (Santa Ana, Calif.).

Preferably, some means should be provided to secure the infusion catheter segments 32 and 34 to the pocket assembly 12 to prevent the tubing from being pulled out of the catheter sleeve 22. For example, if a double-lumen catheter is used, a loop of stitching can be placed through the Y-intersection where the two segments join together. Alternately, an enlarged plastic fitting or grip that is securely affixed to the tubing by means such as glue, heat-bonding, or crimping can be provided as the attachment device. This would allow one or more loops of thread to be wrapped around or passed through the attachment device and through the fabric of the net, by the surgeon.

FIG. 3 shows a cooling net assembly secured around a heart during surgery. For orientation, this figure shows retractor 100, which is used to keep the ribs distended, and sutures 102 which pass through the opened walls of pericardium 104. The aorta 106 and the right atrial appendage 108, which are not covered by the net 10, are also shown. The net pocket 12 is fitted over the ventricular portion of the heart, and the drawstring 28 is placed next to the right atrial appendage 108 and tied in a knot 110.

In FIG. 3, the net is depicted as an open-mesh net for illustration purposes. The preferred fabric, discussed below, has a moderately tight weave interspersed with pores roughly 2 to 4 mm in width or diameter when stretched to fit over a heart. These pores fill with water when the net is saturated during use, providing continuous fluid coverage over the entire surface of the heart.

The net is initially positioned so that short catheter segment 32 is positioned at or near the uppermost surface of the heart. This allows chilled liquid which exits the short segment 32 to diffuse throughout the net in both directions, aided by gravity.

After the net is properly positioned and secured in place, a physiologically-compatible liquid such as saline solution which has been chilled to a desired temperature, such as about 8° to 10° C., is infused into the net 10 through supply tube 46 and short catheter segment 32. This can be done by coupling supply tube 46 to any suitable source of chilled liquid, such as a pumped supply, or a suspended bag which was previously chilled in a refrigerator or freezer, hanging from an intravenous stand.

After the cold liquid leaves the short catheter segment 32 via side holes 33, it diffuses throughout the entire fabric portion of pocket 12, aided by gravity and by capillary flow due to the hydrophilic nature of the fabric. As it passes through the net, the cold liquid directly contacts the surface of the heart, thereby chilling the heart. Since liquid which saturates the net is continuously being displaced by the infusion of more chilled liquid, it drips out of the net and collects in the basin provided by the open pericardium 104. After it leaves the net and collects in the pericardial basin, it is removed from the patient's chest by means of a suction tube.

Figure 4:
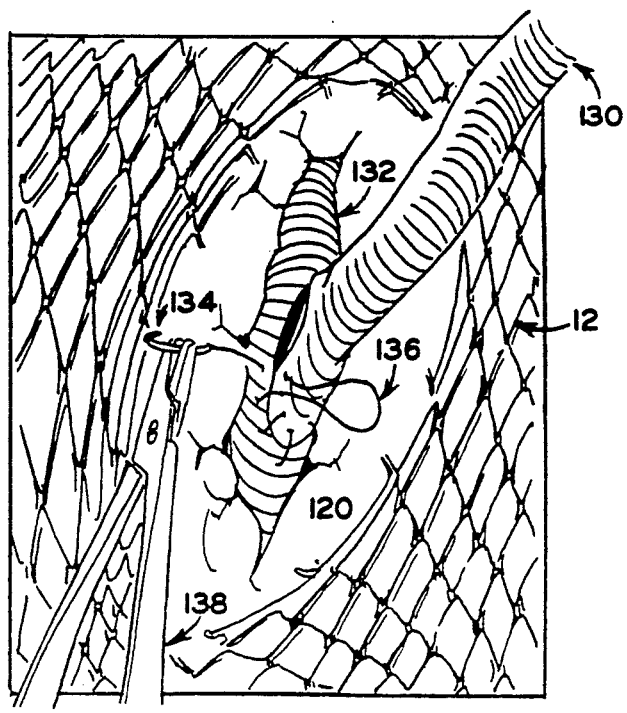
FIG. 4 is a perspective view of a cooling net in use during heart surgery, after a cut has been made in the net to expose a coronary artery.

In order to reach a specific coronary artery which must be operated upon, a cut 120 is made through a part of the net, using scissors 122 or a scalpel if desired. As shown in FIG. 3 and FIG. 4, this exposes the desired region of the heart to the surgeon, without affecting the ability of the net to carry and diffuse cooling water throughout the remainder of the net. FIG. 4 depicts an anastomosis being created during a coronary bypass operation, where a segment of blood vessel 130 taken from elsewhere in the patient's body is being sutured to a coronary artery 132, using needle 134, suture thread 136, and needle holder 138. If desired, a dark stain may be placed on the region of the heart which is to be operated on, using a suitable dye such as methylene blue. The dye will be visible through the mesh of the net, and it will indicate where the surgeon should cut through the fabric.

During surgery, if it is necessary to lift the heart and operate on the rear portions, the bottom apex of the heart will be temporarily positioned at the top of the heart while it is being held up. During that period, the valve 40 is actuated to cause the cold liquid to exit through long catheter segment 34 rather than short segment 32. This would continue to aid in the diffusion of cold saline throughout the entire net, during the entire operation. This approach, although preferred, is not necessarily required; the cooling net of this invention, even if provided with only one infusion catheter, provides a major benefit over the cooling devices and techniques of the prior art and will provide a level of cooling that may regarded as quite adequate by most surgeons.

Figure 6:
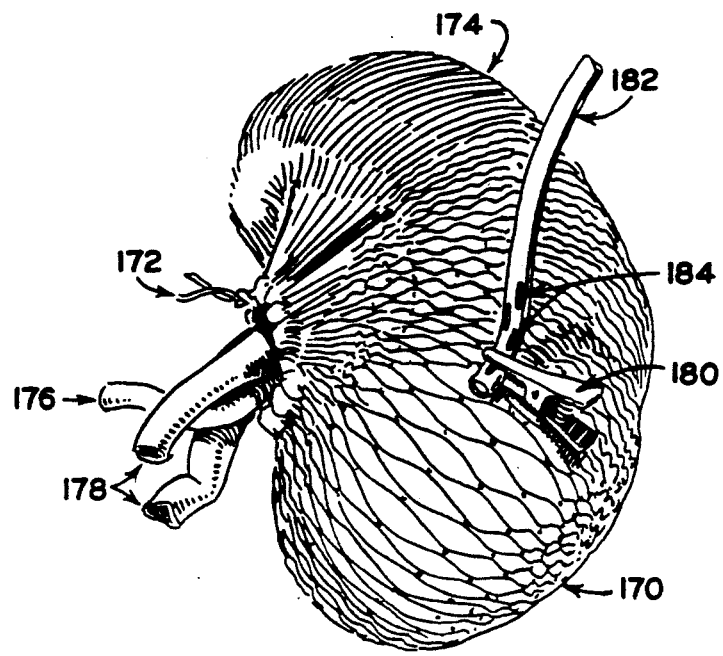
FIG. 6 is a perspective view of a cooling net in use during a kidney transplant operation, showing a method of securing the infusion catheter to the outside of the net.

In an alternate preferred embodiment, one or more infusion catheters can be secured to the outside of the net. For example, as shown in FIG. 6 (which shows a cooling net secured around a kidney), a plastic or metallic alligator clip 180 can be coupled to the catheter 182 at or near the end of the tubing. This can be done by affixing the jaws of the clip to the tubing, as shown; alternatively, a metallic wrap-around attachment device on either handle of clip 180 can be permanently coupled to the end of the tube by wrapping the attachment device around the tube and crimping the metallic prongs onto the tube. During surgery, after the net has been placed in position around the organ, the clip can be affixed to the net, on the outside of the net, at any desired location. If the position of the catheter outlet needs to be changed (for example, while a heart is lifted to obtain access to the posterior region during surgery), the clip 180 can be easily released from one location on the net and moved to a different location.

Preferably, nets having a range of sizes (small to large) should be provided. There is a substantial range of heart sizes in adults, and infant and pediatric surgery extends the range of sizes even more. However, so long as the fit of the net on an organ is reasonably close, it does not need to be exact. The elasticity of the fabric, and the use of a drawstring, elastic strap, Velcro segment, or other securing device that can be adjusted when the net is secured in place will allow a net to be conformingly fitted onto hearts having a range of sizes.

Criteria for the Fabric of the Net

The front and back walls of the net are made of a porous, water-permeable fabric which preferably should have three characteristics that will increase its suitability for use as described herein.

First, since human organs vary considerably in size, the material preferably should be elastic in the direction of both the warp and the woof, to encourage close conformance of the net to the surfaces of an organ during surgery. However, non-elastic material can be used with adequate results if desired, particularly if nets of various sizes are available.

Second, the fabric should be made of hydrophilic material, to encourage capillary diffusion of water throughout the entire net during use. This characteristic can be easily determined for any material by dipping one corner of a piece of fabric into a bowl or glass of water. If the fabric is hydrophilic, it will begin acting as a wick, and water will rise up into the fabric above the water level in the bowl or glass. Alternately, if a cooling liquid other than an aqueous solution is used, then the fabric should have an affinity for that particular liquid.

Third, the material should retain its overall structural integrity even if a cut is made in a portion of the material. As shown in FIG. 4, after a net has been secured in place around a heart for a coronary bypass operation, the artery being operated on will be exposed by cutting through the fabric of the net in the desired location. That incision must be limited to the cut that is made by the surgeon; it must not cause a self-propagating tear (a "run") in the fabric that will extend beyond the desired incision.

A suitable material which meets all of those criteria, and which has been used with good results in several prototypes, is sold by Southern Webbing Mills, Inc., of Greensboro, N.C. It is called "elastic mesh fabric" by the supplier. The suitability of any other candidate fabric which appears to meet the operating requirements of the subject invention can be determined by routine testing for elasticity, hydrophilicity, and tear-resistance. In addition, fabrics which do not currently meet the structural integrity (anti-running or rip-stopping) requirement of this invention can be modified to make them suitable, by means such as providing reinforcing strands at spaced intervals in the fabric, in a manner comparable to the "rip-stop" nylon fabric used in many tents and sleeping bags.

Atrial Cooling

In a preferred embodiment of a cooling net for use during heart surgery, the cold saline solution passes through a segment of tubing with permeable walls, referred to herein as atrial cooling segment 44. This segment 44 can be incorporated into the supply tube 46 as shown in FIGS. 1 and 5; alternately, an atrial cooling tube can be provided as a separate tube if desired, provided that some means is provided for simultaneously supplying cold liquid to both the atrial cooling tube and the rest of the catheter assembly 30.

Figure 5:
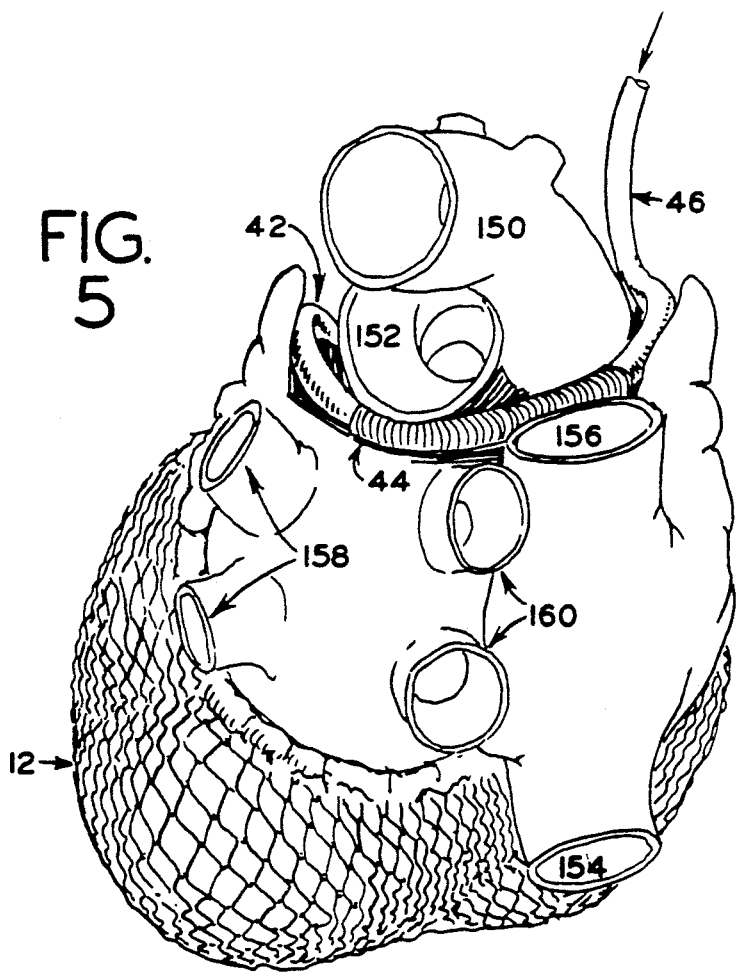
FIG. 5 is a perspective view of a cooling net being used during heart surgery, shown from the rear of the heart, indicating the placement of the atrial cooling segment.

During surgery, the atrial cooling segment 44 is positioned next to the atrial region of the heart, in the transverse sinus, as shown in FIG. 5. For orientation, FIG. 5 indicates the positions of aorta 150, pulmonary artery 152, inferior vena cava 154, superior vena cava 156, left pulmonary veins 158, and right pulmonary veins 160.

The positioning of atrial cooling segment 44 in the transverse sinus allows cold liquid exiting the atrial cooling segment 44 to chill the atrial region of the heart, while the remainder of the cold liquid permeates throughout net 12 and chills the ventricular portion of the heart. Depending on the length and permeability of the porous segment, a substantial portion (up to about half) of the cold solution diffuses out of the tube through the atrial cooling segment 44.

In several prototypes that have been made and tested on humans, porous and permeable segments made of about 2 to 3 cm of woven Dacron (a trademark of DuPont) performed quite adequately. Various other types of fabric which are permeable to water are known and can be used as described herein. Alternately, a segment of normally impermeable tubing can be used if small holes or slits are made through the tubing material. This would simplify manufacturing: the atrial cooling segment could be made merely by punching holes into a limited segment of a single piece of tubing, allowing a single piece of tubing to function as segments 42, 44, and 46 shown in FIG. 1.

Use of External Water Supply

An alternate embodiment of this invention would eliminate the need for providing any infusion tubing within the net or as part of a surgical kit. Although this approach is less than optimal from an operational viewpoint, it would simplify the construction of the net while providing substantially better performance than other methods widely used today.

As with the continuous infusion option, this option would enclose the heart (or other organ, as described below) in a permeable fabric net, wherein one or more openings can be cut in the net to render portions of the surface of an organ accessible, as described above. The sole difference is that cold saline solution could be intermittently supplied from an external source. For example, a surgical assistant holding a small pitcher or a supply tube coupled to a refrigeration unit could gently flush cold solution over the net, either continuously or on a frequent basis. In contrast to the intermittent slush method, the permeable net would diffuse and distribute the cold liquid and keep the liquid in close and effective cooling contact with the entire surface area that is covered by the net. It would require only a second or two to pour a sufficient quantity of water across the exposed surface of the net to allow it to function effectively, and the surgical work could resume as soon as the pouring action is completed instead of having to stop and wait for a large quantity of slush or cold water to exert its effects and then sucking out the slush or water before proceeding with the surgery.

As mentioned above, this approach is not the optimal approach from a surgeon's perspective, since a surgeon would prefer continuous infusion with no disruptions. Nevertheless, it is a substantial improvement over the prior art and can provide effective cooling with far less disruption and delay than the intermittent slush method currently in use.

Nets for Transplanting Organs

Since the cooling net of this invention provides an effective and adaptable method of cooling which does not impede access to an organ during surgery, this device can also be used during transplant surgery, not just on hearts, but also on other organs including kidneys, livers, lungs, and pancreases. As an example, FIG. 6 shows a cooling net 170 secured using drawstring 172 around kidney 174. The drawstring 172 does not interfere with access to ureter 176 or the blood vessels 178.

The method of using a net during an organ transplant is essentially identical as described above during heart surgery. The net is secured around the organ and cold liquid is infused into the fabric. The liquid diffuses through the fabric and directly contacts the organ, chilling the organ. As the liquid drips out of the net into the patient's chest or abdominal cavity, it is removed by means of a suction tube.

Although the nets described above for use during heart surgery can be used without modification during heart transplants, certain adaptations should be made to the nets in order to render them more suitable for use on other organs. The first adaptation involves size and shape. A net should be suitably sized and shaped for the organ it will be used on, and a net meant for a kidney would be too small for use on an adult lung. Accordingly, nets that are designed and sized for a certain organ should be provided for each different type of organ listed above, and a range of sizes for each type of organ should be provided, to allow them to be used on both adults and children of all ages. However, as mentioned above with regard to nets for heart surgery, an exact size match is not essential; elastic material and adaptable securing devices will allow a certain net to be used on organs having a substantial range of sizes.

The second adaptation involves the number and positioning of the infusion catheters. For some types of organ transplants, such as a kidney implantation as shown in FIG. 6, a net 170 having a single infusion catheter 182 having an internal diameter of about 1 mm or less will be adequate. During surgery, the net 170 preferably should be positioned so that exit holes 184 of infusion catheter 182 are on top of the kidney 172. This will help ensure that the infused liquid will disperse away from the catheter in both directions and cool the entire surface of the organ.

As mentioned previously, FIG. 6 depicts an infusion catheter 182 which is temporarily affixed to the outside surface of a net 170 by means of a securing device such as alligator clip 180, which is clipped to both the catheter 182 and the fabric of the net.

For large organs such as lungs, the number of infusion catheters and/or their diameter can be increased, so that a single large catheter or two or more catheters can carry any desired quantity of water.

Sterile Packaging Material

This invention also relates to an article of manufacture comprising a net assembly (including the securing means, such as a drawstring, Velcro segments, etc.) as described above, stored inside a sealed package which maintains the sterility of the net. If desired, the infusion catheter(s) can be emplaced in the net before packaging, so that the net will be ready for use when the package is opened. Alternately or additionally, the package can contain one or more components that can be assembled for use by the surgical team; such collections of components which are packaged together are commonly called kits, and are widely used in surgery.

Figure 7:
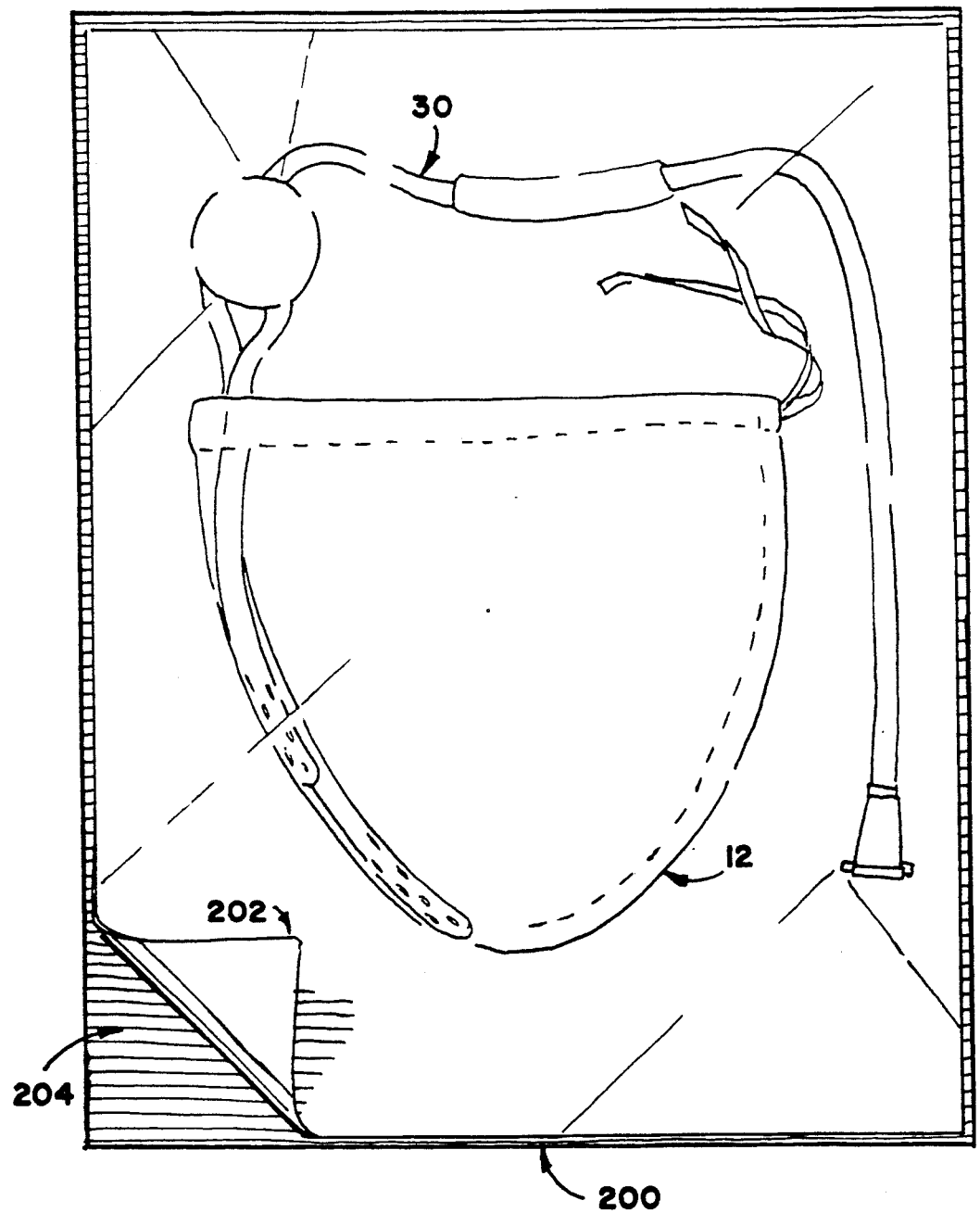
FIG. 7 is a perspective view of a cooling net inside a sealed plastic package which maintains the sterility of the net.

A package 200 containing a net 12 designed for heart surgery, with a catheter assembly 30 is shown in FIG. 7. The package 200 preferably is an airtight, watertight sealed plastic pouch. A transparent front layer 202 (which is shown partially opened at one corner, for illustration purposes) enables the user to quickly identify or confirm the contents. Until the package is opened, the front layer 202 is sealed around the entire periphery of the package to a back layer 204, which can be either opaque or transparent. The two sealed layers form a relatively flat envelope which is impervious to water, air, bacteria, and viruses.

Any type of packaging material which is conventionally used to store sterile surgical instruments or devices can be used, such as plastic which is permeable to a sterilizing gas such as ethylene oxide, or plastic which will withstand the temperatures used in autoclaves.

The entire article of manufacture (i.e., the packaging material and the enclosed net and catheters) can be sterilized in any manner suitable to render the net safe for use during surgery, such as by means of ethylene oxide or by high temperature. Ionizing radiation that can penetrate fabric can be used for sterilization if desired; however, ultraviolet radiation is not preferred, since the fabric of the net might provide bacteria or viruses with niches that would not receive enough radiation to ensure sterility.

After sterilization, the sealed package will maintain the sterility of the enclosed net even if the outside of the package becomes soiled.

Thus, there has been shown and described an improved device and method for cooling internal organs during surgery, which fulfills all the objects and advantages set forth above. It will be apparent to those skilled in the art that various changes and modifications to the specific embodiments described herein are possible. Any such changes that do not depart from the spirit and scope of the invention are deemed to be covered by the invention, which is limited only by the claims which follow.

REFERENCES

Bonchek, L. I. and Olinger, G. N., "An improved method of topical cardiac hypothermia," J. Thorac. Cardiovasc. Surg. 82: 878–882 (1981)

Daily, P. O., et al, "Clinical comparisons of methods of myocardial protection," J. Thorac. Cardiovasc. Surg. 93: 324–336 (1987)

Daily, P. O., et al, "Comparison of myocardial temperatures with multidose cardioplegia versus single-dose cardioplegia and myocardial surface cooling during coronary artery bypass grafting," J. Thorac. Cardiovasc. Surg. 97: 715–724 (1989)

Daily, P. O. and Kinney, T. B., "Optimizing myocardial hypothermia: II. Cooling jacket modifications and clinical results," Annals Thorac. Surg. 51: 284–289 (1991)

Rosenfeldt, F. L. and Watson, D. A., "Local cardiac hypothermia: Experimental comparison of Shumway's technique and perfusion cooling," Annals Thorac. Surg. 27: 17–23 (1978)

Rousou, J. A. and Breyer, R. H., "Phrenic nerve paresis associated with the use of iced slush and the cooling jacket for topical hypothermia," J. Thorac. Cardiovasc. Surg. 89: 921–925 (1989)

Shumway, N. E. and Lower, R. R., "Topical cardiac hypothermia for extended periods of anoxic arrest," Surgical Forum 10: 563–566 (1959)

We claim:

1. A device for cooling an internal organ during surgery, comprising:
   a. a net made of a water-permeable fabric having a size and shape that allow the net to be fitted in a conforming manner around at least a portion of the organ; and
   b. a conduit having (1) an inlet adapted to be coupled to a source of a chilled liquid during use, and (2) at least one outlet for the chilled liquid to exit the conduit, wherein, when the net is in use during surgery, at least one outlet of the conduit is in fluid communication with the fabric of the net and positioned in a manner which directs chilled liquid exiting the conduit through said outlet into the fabric of the net, thereby causing the liquid to permeate into and diffuse through the fabric of the net so that the chilled liquid will contact the surface of the organ.

2. The device of claim 1 wherein the net further comprises a sleeve which extends along a portion of the net and wherein the outlet of the conduit is comprised of a permeable segment wherein a plurality of holes pass through the permeable segment, and wherein the permeable segment of the conduit is held within the sleeve.

3. The device of claim 1 wherein the fabric is made of hydrophilic fibers and wherein the fabric is elastic.

4. A device for cooling a heart during surgery, comprising:
  a. a net made of a water-permeable fabric having a size and shape that allow the net to be fitted in a conforming manner around at least a portion of the heart and,
  b. a conduit having (1) an inlet adapted to be coupled to a source of a chilled liquid during use, and (2) at least one outlet for the chilled liquid to exit the conduit, wherein, when the net is in use during surgery, at least one outlet of the conduit is in fluid communication with the fabric of the net and positioned in a manner which directs chilled liquid exiting the conduit through said outlet into the fabric of the net, thereby causing the liquid to permeate into and diffuse through the fabric of the net so that the chilled liquid will contact a surface of the heart, and wherein a cut can be made in the fabric to expose a portion of the surface of the heart without substantially altering the ability of the net to convey the chilled liquid to other portions of the surface of the heart.

5. The device of claim 4 comprising two conduits having fluid outlets which can be positioned adjacent to different areas on the surface of the heart.

6. The device of claim 4 which contains, within the conduit, a permeable atrial cooling segment positioned at a location in the conduit which allows the atrial cooling segment to be placed adjacent to an atrial region of the heart, in a manner such that when the device is in use and the atrial cooling segment is positioned in the atrial region, chilled liquid will emerge from the atrial cooling segment and contact the atrial region of the heart.

7. An article of manufacture comprising packaging material and a net for cooling an internal organ during surgery, wherein the net is made of a water-permeable fabric having a size and shape that allow the net to be fitted in a conforming manner around an internal organ, and wherein the net is provided with a securing device which allows the net to be secured around at least a portion of the organ, and wherein the net and securing device are enclosed within the packaging material, and wherein the article of manufacture has been sterilized, and wherein the packaging material maintains the sterility of the net and securing device until the packaging material is opened.

8. The article of manufacture of claim 7 wherein the net further comprises a sleeve which extends along a portion of the net and wherein a conduit having an inlet adapted to be coupled to a source of chilled liquid is securely affixed within the sleeve in the net.

9. The article of manufacture of claim 7 wherein the packaging material also contains a sterilized conduit having an inlet that can be coupled to a source of chilled liquid, and an outlet region adapted to be affixed to the net in a manner such that chilled liquid which exits the outlet region will be directed into the net.

10. A method of chilling an internal organ during surgery, comprising the following steps:
  a. securing a net made of water-permeable fabric in a conforming manner around at least a portion of an internal organ;
  b. infusing a chilled liquid into the fabric of the net so that the chilled liquid will permeate throughout the fabric of the net and directly contact the surface of the organ, thereby chilling the organ.

11. The method of claim 10 wherein the internal organ is a heart, and wherein the chilled liquid is infused into the net by means of a conduit affixed to the net, and wherein the conduit comprises a permeable atrial cooling segment which is positioned during surgery adjacent to an atrial region of the heart in a manner such that when chilled liquid flows through the conduit, a portion of the chilled liquid emerges from the atrial cooling segment of the conduit and contacts the atrial region of the heart.

12. A method of chilling a heart during coronary bypass surgery, comprising the following steps:
  a. securing a net made of water-permeable fabric in a conforming manner around at least a portion of the heart;
  b. infusing a chilled liquid into the fabric of the net so that the chilled liquid will permeate throughout the fabric of the net and directly contact a surface of the heart, thereby chilling the heart;
  c. cutting an opening in the net to expose a surface of the heart in an exposed region surrounding an artery that needs to be bypassed; and,
  d. continuing to infuse the chilled liquid into the fabric of the net so that surfaces of the heart that remain in contact with the net in areas other than the exposed region will continue to be cooled by the chilled liquid.

13. The method of claim 12 wherein the chilled liquid is infused into the net by means of a conduit affixed to the net, and wherein the conduit comprises a permeable atrial cooling segment which is positioned during surgery adjacent to an atrial region of the heart in a manner such that when chilled liquid flows through the conduit, a portion of the chilled liquid emerges from the atrial cooling segment of the conduit and contacts the atrial region of the heart.

* * * * *